United States Patent [19]

Sessions et al.

[11] Patent Number: 5,605,165
[45] Date of Patent: Feb. 25, 1997

[54] WOUND MEASURMENT DEVICE AND METHOD FOR ITS USE

[75] Inventors: Robert W. Sessions, Hinsdale; Roy D. Carr, Burr Ridge; Rainer Schmeichel, Glen Ellyn, all of Ill.

[73] Assignee: Ferris Corp., Burr Ridge, Ill.

[21] Appl. No.: 398,225

[22] Filed: Mar. 3, 1995

[51] Int. Cl.⁶ ........................................... A61F 5/37
[52] U.S. Cl. ........................ 128/888; 602/41; 602/47
[58] Field of Search .................... 128/887, 888; 602/41–46, 52–58; 604/304, 307

[56] References Cited

U.S. PATENT DOCUMENTS

| | | | |
|---|---|---|---|
| 4,341,207 | 7/1982 | Steer | 602/47 |
| 4,867,150 | 9/1989 | Gilbert | 602/47 |
| 5,000,172 | 3/1991 | Ward | 128/888 |
| 5,176,663 | 1/1993 | Svedman | 128/888 |
| 5,266,605 | 11/1993 | Afflerbach | 602/42 |

*Primary Examiner*—Michael A. Brown
*Attorney, Agent, or Firm*—Leydig, Voit & Mayer, Ltd.

[57] ABSTRACT

Device and related method for determining the surface area of a wound. The device includes a transparent sheet having a series of perforations defining first and second sections of the sheet which allow the first and second sections to be separated from one another along the perforations. The transparent sheet is folded along the perforations so that the two sections overlap each other, and the sections are substantially free of adhesive material. The second section includes indicia thereon which allow a user to determine the surface area of a wound after the outline of the wound or opening is traced thereon. Upon use, the device is placed over the wound or opening, with the first section toward the wound or opening, and the outline of the wound or opening is traced onto the second section. The second section containing the marked outline of the wound, which was isolated or shielded from contact with the wound, is then separated from the first section along the perforations, allowing the second section to be immediately handled by a person, i.e., without subjecting the second section to cleaning or sterilization.

17 Claims, 2 Drawing Sheets

{ 5,605,165 }

WOUND MEASURMENT DEVICE AND METHOD FOR ITS USE

TECHNICAL FIELD OF THE INVENTION

The present invention relates to devices for measuring the surface area of a wound or opening in an animal, and methods for their use.

BACKGROUND OF THE INVENTION

In the care of patients afflicted with wounds to the flesh, such as, cuts, burns, bruises, ulcerations, lacerations, and the like, the extent of wound healing over time is monitored by measuring the surface area of the wound on a regular, periodic basis. Further, the proper evaluation of wound management products and therapies also requires the extent of wound healing to be monitored on a regular, periodic basis.

Wound monitoring, both for determining healing and the effectiveness of wound management products, has traditionally involved first recording the surface area of the untreated wound on a single transparent plastic sheet. Printed on one side of that sheet is wound sizing indicia, e.g., a grid or bulls-eye. The area of the wound is typically recorded by simply placing that printed sheet over the wound, and tracing the outer boundary, or periphery, of the wound with a suitable marking device. After marking, any wound debris remaining on the sheet is removed, e.g., by wiping with a suitable disinfecting or sterilizing cleanser. The size of the wound is then determined by comparing the marking with the sizing indicia. The marked sheet, which now contains a sized, graphical representation of the wound, is then placed into the patient's file for future reference.

The foregoing procedures, when repeated over a period of time, e.g., daily, creates an accurate wound history for that patient. A number of these histories assembled from different patients can be used to compare the effectiveness of new wound management products and therapies with those currently available. As a general rule, a product which effects the greatest decrease in wound area over a given period of time would be deemed more desirable as compared to a product that effected a lesser decrease in wound area over that same period of time.

The use of presently available wound marking devices, however, creates potentially serious problems for the clinician. As the device is placed over the wound, the side which faces the open wound often becomes contaminated with wound exudate, blood, necrotic tissue, and the like. Contaminated devices must be cleaned and dried, and in most cases sterilized, before they can be safely handled without gloves, or stored, e.g., in a patient's file. Contaminated devices are especially dangerous when the device has been used on a patient who has a contagious disease, such as, HIV, hepatitis, or on a patient whose body fluids harbor other types of infectious agents.

One device which purports to overcome at least the contamination problem mentioned previously is described in U.S. Pat. No. 5,265,605. This device comprises two separate transparent sheets, one being a backing sheet and the second consisting of the wound assessment sheet. The back of the wound assessment sheet is coated with an adhesive which allows it to remain tacked to the backing sheet until after the wound assessment is completed, wherein the sheets are manually separated. The device is further designed so that, after it is placed over a wound and an outline of the wound is traced thereon, the wound assessment sheet is peeled from the backing sheet and is subsequently secured onto a wound assessment worksheet by the adhesive which remains on the back of the assessment sheet. The worksheet is then placed in the patient's file for future reference.

While the foregoing device purportedly avoids contamination of the assessment sheet, it has certain drawbacks. One of these is that a caregiver is unable to place two or more assessment sheets on top of each other to directly compare one wound assessment with another because the sheets have an adhesive thereon, and further because such sheets are said to be adhered onto an assessment worksheet after use. This type of comparison is extremely helpful to a caregiver, enabling one to accurately compare the effects of wound treatment over time. Moreover, the device described in the '605 patent does not take into consideration the real-life problem of caregivers who do not center the wound with respect to the assessment grid in precisely the same manner each time an assessment is undertaken. If one is unable to superimpose one assessment sheet upon another, the lack of a centered assessment complicates the accurate evaluation of wound size.

It is therefore a primary object of the present invention to provide a device and method for wound monitoring that enables the surface area of a wound to be determined, while minimizing a clinician's risk of exposure to contagious or infectious agents present in the wound exudate.

It is a further object of the present invention to provide a device and method for wound monitoring which provide a relatively quick means for removing any wound debris remaining on a device that has come into contact with the wound during use.

A related object of the present invention is to provide a device and method that will reduce the amount of time it takes a clinician to obtain a clean, exudate-free, record of the surface area of a patient's wound.

Yet another object of the present invention is to provide a device and method with the aforementioned features while allowing one to easily and accurately compare of a series of wound assessments.

A further object of the present invention is to provide a device which has the foregoing features, but which is relatively economical to manufacture.

These and other objects and advantages of the present invention, as well as additional inventive features, will be apparent from the description of the invention provided herein.

SUMMARY OF THE INVENTION

The present invention provides a device and method for recording, and thereby measuring, the surface area of a wound, or an opening, in an animal. The device and method of the present invention offer vastly improved performance over known devices and methods, particularly in the areas of user safety and ease-of-use, and further provides the advantage of allowing one view simultaneously, and thereby accurately contrast and compare, a series of wound assessments. Moreover, the device is lower in cost as compared with certain known wound assessment devices.

The device of the present invention comprises a transparent sheet having a series of perforations defining first and second sections of the sheet which allow the first and second sections to be separated from one another along the perforations. The second section further includes an indicia thereon which allows a user to determine the surface area of a wound. In addition, the transparent sheet is folded along the perforations so that the two sections overlap each other, the sections being substantially free of adhesive material.

Another aspect of the present invention is a method for recording the surface area of a wound or opening in the body of an animal. This method comprises applying to the wound or opening the transparent device of the present invention. Upon use, the device, which may be provided as a sterile product if desired, is placed over the wound so that the second section is isolated from the wound by the first section. The user then marks the second section to indicate the surface area of the wound, i.e, by drawing a line along the outer edges, or periphery, of the wound. After the marking is completed, the first and second sections may be separated from one another along the perforations. In this way, the first section, which contacted at least the skin surrounding the wound, and very likely the wound itself, may be discarded. The second section, which was isolated or shielded from contact with the wound specifically, and the patient generally, may be immediately handled by a person even without protective gear, e.g., without the use of gloves. In other words, no cleaning, sterilizing, or drying of the second section (which contains the marked outline of the wound) is required. Alternatively, the second sheet, which is free of any contagious or infectious contaminants, may be immediately placed into a patient's file for later review by a physician without fear of contaminating either the file or the physician.

The device, being substantially free of adhesive material, allows one to easily superimpose a series of marked second sections over one another. This enables a caregiver to directly, and accurately, compare the size of the wound over time. Further, the device is easier to handle because it will not adhere to a surface with which it comes into contact. In addition, the device is less costly to prepare than devices which require the inclusion of adhesive thereon.

The present invention may best be understood with reference to the following detailed description of the preferred embodiments.

DESCRIPTION OF THE PREFERRED EMBODIMENTS

The present invention provides a device and method for recording, and thereby measuring, the surface area, or size, of a wound or opening in the tissue of an animal. While it is expected that the device and method will primarily be used in connection with injuries to humans, they are equally applicable to any animal, domesticated or wild, land- or sea-dwelling.

Figure 1:
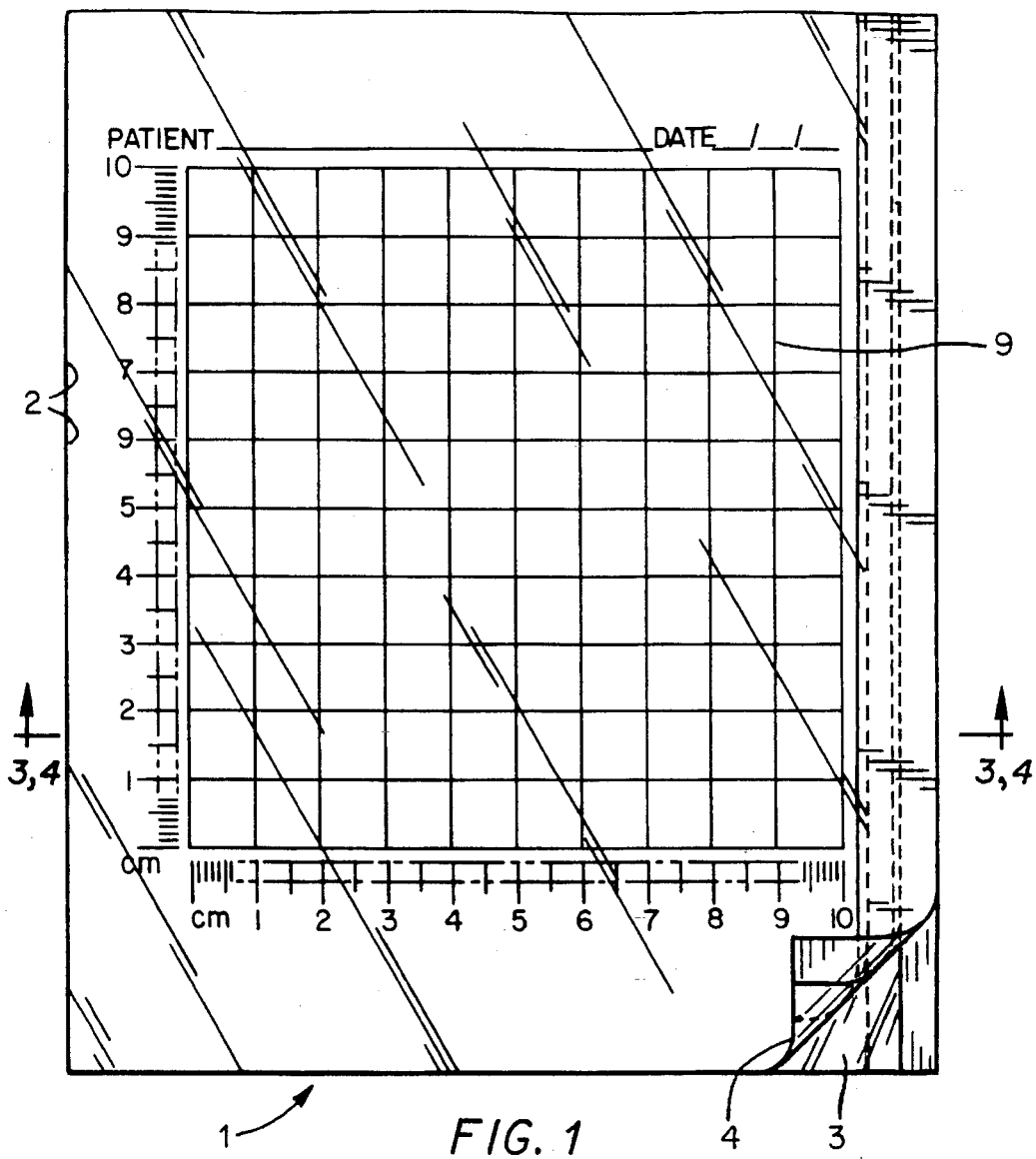
FIG. 1 is a top view of one embodiment of the device of the present invention wherein the first and second sections have been folded along perforations so that the two sections overlap one another, the embodiment further including indicating tabs.
Figure 2:
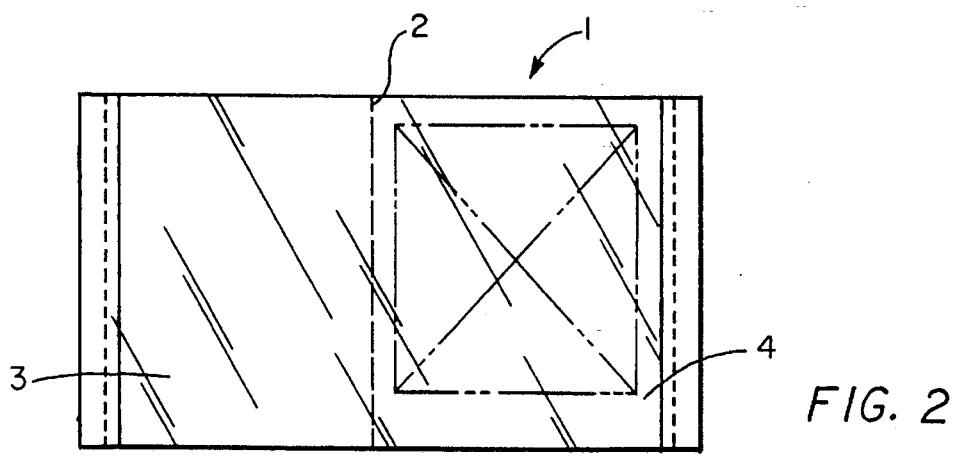
FIG. 2 is a cross-sectional view of the embodiment illustrated in FIG. 1 prior to folding of the sheet along its perforations to provide the device illustrated in FIG. 1.

The device of the present invention may be better understood by reference to FIG. 2. This. figure is a top view of one embodiment of the inventive device prior to being folded upon itself to provide the configuration set forth in FIG. 1. FIG. 2 shows the device generally comprising a transparent sheet 1 having a series of perforations 2 defining first 3 and second 4 sections of the sheet which allow the first 3 and second 4 sections to be separated from one another along the perforations 2 when desired. As shown in FIG. 1, the transparent sheet is folded along the perforations 2 so that the two sections 3, 4, overlap each other.

Figure 3:
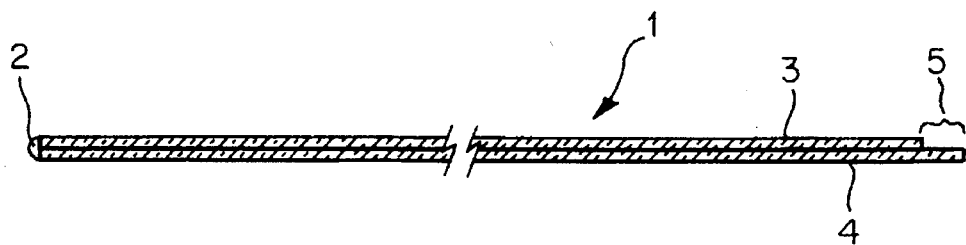
FIG. 3 is another embodiment of the device of the present invention wherein a side view of the device of FIG. 1 the present invention is illustrated without indicating tabs.

Advantageously, the transparent sheet 1 is rectangular or square in shape, and the perforations extent along one of its midlines. Preferably, however, and as best illustrated in FIG. 3, the perforations are made to one side of a midline of the transparent sheet. In this manner, one section is not coterminal with the other, e.g., one edge of a section extends beyond the other, most preferably the first section 3. This provides a user with a tab 5, which eases separation of the sections from one another after an assessment is completed.

The transparent sheet may comprise any of a number of materials. However, the transparent property of the sheet is important to the proper functioning of the device. Because the device is designed to be placed over a wound or opening, the wound or opening must be able to be seen through the two sections of the sheet. If the wound or opening cannot be seen, the desired accurate tracing of its periphery cannot be obtained.

The sheet should comprise a material which is non-permeable to liquids. This assists in ensuring that no liquid from the wound situs is transmitted through the first sheet and onto the second sheet, resulting in contamination of the second sheet.

Moreover, the sheet is advantageously sufficiently flexible to allow the device to follow the contours of the body over which it is placed upon use. the sheet should also be able to accept and retain a mark placed upon it during tracing of the wound periphery.

Sheet materials which are preferred for use in the inventive device include polypropylene, polyethylene, polyvinylchloride, polyester, polystyrene, and acetate. These materials are able to be prepared so that they are transparent, flexible, and liquid-impermeable.

The device should further provide some type of indicia which allows a user to measure or otherwise analyze the size of the wound after the assessment is completed. A bullseye indicia may be used or, as illustrated in FIG. 1, a grid 9 may be used. In any event, the indicia is should be printed onto the second section 4 of the device, using any type of suitable ink. Preferably, an ink which is non-toxic may be used.

Figure 4:
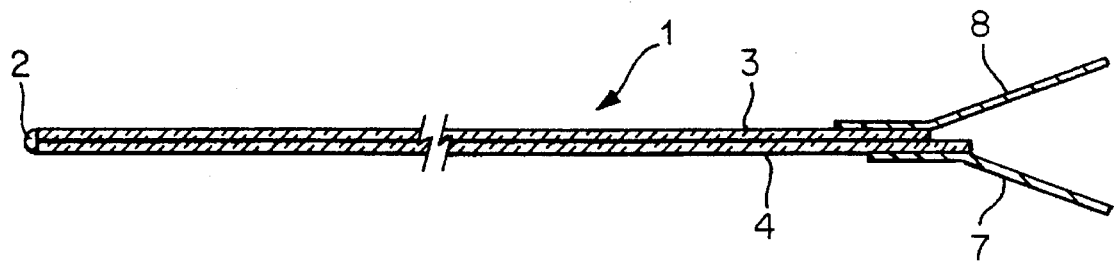
FIG. 4 is a side view of the embodiment illustrated in FIG. 1.

As a further means of assisting in the separation of the first and second sections, at least one of the sections may include an indicating tab, e.g., 7 of FIG. 4, which is adhered in any conventional manner to a desired section. As FIG. 7 illustrates, such tabs contain no adhesive on their exposed surface. This allows a user to easily separate and grasp both first and second sections when separation is desired. Preferably, however, both first and second sections will include an indicating tab, as shown by indicia 7 and 8 in FIG. 4.

The sheet, and therefore the sections, should be substantially free of adhesive material (except that which is used to attach any indicating tab to one or both sections), e.g., a glue or resinous adhesive. The inclusion of such adhesive material would only serve to hinder the separation of the first and second sections from one another after the wound or opening has been traced on the device.

However, a temporary adhesive-like effect, i.e., which effect is not present after the sections are separated from each other after the device is used, may advantageously be provided to at least a portion of the first and second sections by heating the first and second sections, or a portion thereof, while a portion of those sections are in contact with each other, by cold edge pattern sealing the sections, or by hot edge pattern sealing the sections. The processes for providing the aforesaid temporary adhesive-like effect are well-known to those skilled in the art, and will therefore not be further described herein. Such temporary "adhesion" is advantageous in that it prevents the two sections from moving, e.g., sliding, relative to one another while a user traces a wound onto the device, such slippage potentially introducing errors into the assessment.

It is also desirable that the device of the present invention be capable of being sterilized. Sterilization is preferred because maintaining a wound as sterile as possible is of significant importance in the healing process. If such sterilization is desired, the sheet material should be selected so that the performance of the final sterilized device is not unduly adversely affected.

In a second aspect of the present invention, there is provided a method for determining the area of a wound or opening in an animal. In accordance with this aspect of the invention, a transparent device of the present invention is placed over the wound or opening so that the second section is isolated from the wound or opening by the first section. After the device is properly positioned, the second section is marked to indicate the surface area of the wound or opening by tracing its periphery. After the second section is marked, the first and sections, which are preferably free of any adhesive material therebetween, are separated from one another by tearing along the perforations. The first section, which has at least contacted the patient's skin, and in all likelihood the wound itself, is discarded. The second section, which did not contact any part of the patient, may then be viewed or stored for future use without fear of contaminating either the storage means, e.g., a file, or any one who subsequently contacts the sheet.

All of the references cited herein are hereby incorporated in their entireties by reference.

While this invention has been described with an emphasis upon one or more preferred embodiments, it will be obvious to those of ordinary skill in the art that variations of the preferred devices and methods may be used and that it is intended that the invention may be practiced otherwise than as specifically described herein. Accordingly, this invention includes all modifications encompassed within the spirit and scope of the invention as defined by the following claims.

What is claimed is:

1. A method for recording the surface area of a wound or opening in the tissue of an animal comprising placing a transparent device on the wound or opening, the transparent device comprising a transparent sheet having perforations defining first and second sections of the sheet which allow the first and second sections to be separated from one another along the perforations, the second section having an indicia thereon which allows a user to determine the surface area of the wound or opening, and the transparent sheet being folded along the perforations so that at least a portion of the two sections overlap and contact each other, wherein the portion of the first and second sections which contact each other are substantially free of adhesive material and the device is oriented with respect to the wound or opening so that the second section is isolated from the wound or opening by the first section, and marking the second section to indicate the surface area of the wound.

2. The method according to claim 1, wherein the marked second section is separated from the first section by tearing along the perforations.

3. The method of claim 1, wherein the transparent sheet is substantially free of adhesive.

4. A device for recording the surface area of a wound or opening in the tissue of an animal comprising a transparent polymer sheet having a series of perforations defining first and second sections of the sheet which allow the first and second sections to be separated from one another along the perforations, the second section having an indicia thereon which allows a user to determine the surface area of a wound, the transparent polymer sheet being folded along the perforations so that at least a portion of each first and second section overlap and contact one another, the sections being substantially free of adhesive material therebetween.

5. The device according to claim 4, wherein the transparent polymer is selected from the group consisting of polypropylene, polyethylene, polyvinylchloride, polyester, polystyrene, and acetate.

6. The device according to claim 5, wherein at least one of the sections includes an indicating tab.

7. The device according to claim 6, wherein both first and second sections include an indicating tab.

8. The device according to claim 4, wherein the perforations are located on the sheet so that the sections are not coextensive with each other after the sheet is folded along the perforations.

9. The device according to claim 4, wherein at least a portion of the first and second sections are temporarily adhered to one another by heating the sections while at least a portion of the first section is in contact with at least a portion of the second section, by cold edge pattern sealing the sections, or by hot edge pattern sealing the sections.

10. The device of claim 4, wherein the transparent sheet is substantially free of adhesive.

11. A method for recording the extent of a wound or opening in the tissue of an animal comprising placing a transparent device on the wound or opening, the transparent device comprising a transparent sheet having perforations defining first and second sections of the sheet which allow the first and second sections to be separated from one another along the perforations, the transparent sheet being folded along the perforations so that at least a portion of each first and second section overlap and contact one another, and the device being oriented with respect to the wound or opening so that the second section is isolated from the wound or opening by the first section, and marking the second section to indicate the extent of the wound or opening.

12. The method of claim 12, wherein the marked second section is separated from the first section by tearing along the perforations.

13. The method of claim 12, wherein the portions of the first and second sections which contact one another when the first and second sections are folded along the perforations are substantially free of adhesive.

14. The method of claim 13, wherein the transparent sheet is substantially free of adhesive.

15. A device for measuring the extent of an opening comprising a transparent sheet having perforations defining first and second sections of the sheet which allow the first and second sections to be separated from one another along the perforations, the transparent sheet being folded along the perforations so that the two sections overlap and contact one another, and at least one of the first or second section having an indicia thereon which allows a user to determine the extent of the opening.

16. The device of claim 15, wherein the portions of the first and second sections which contact one another when the first and second sections are folded along the perforations are substantially free of adhesive.

17. The method of claim 16, wherein the transparent sheet is substantially free of adhesive.

* * * * *